April 16, 1940. P. DOT Plant Pat. 378
ROSE PLANT
Filed Aug. 10, 1939
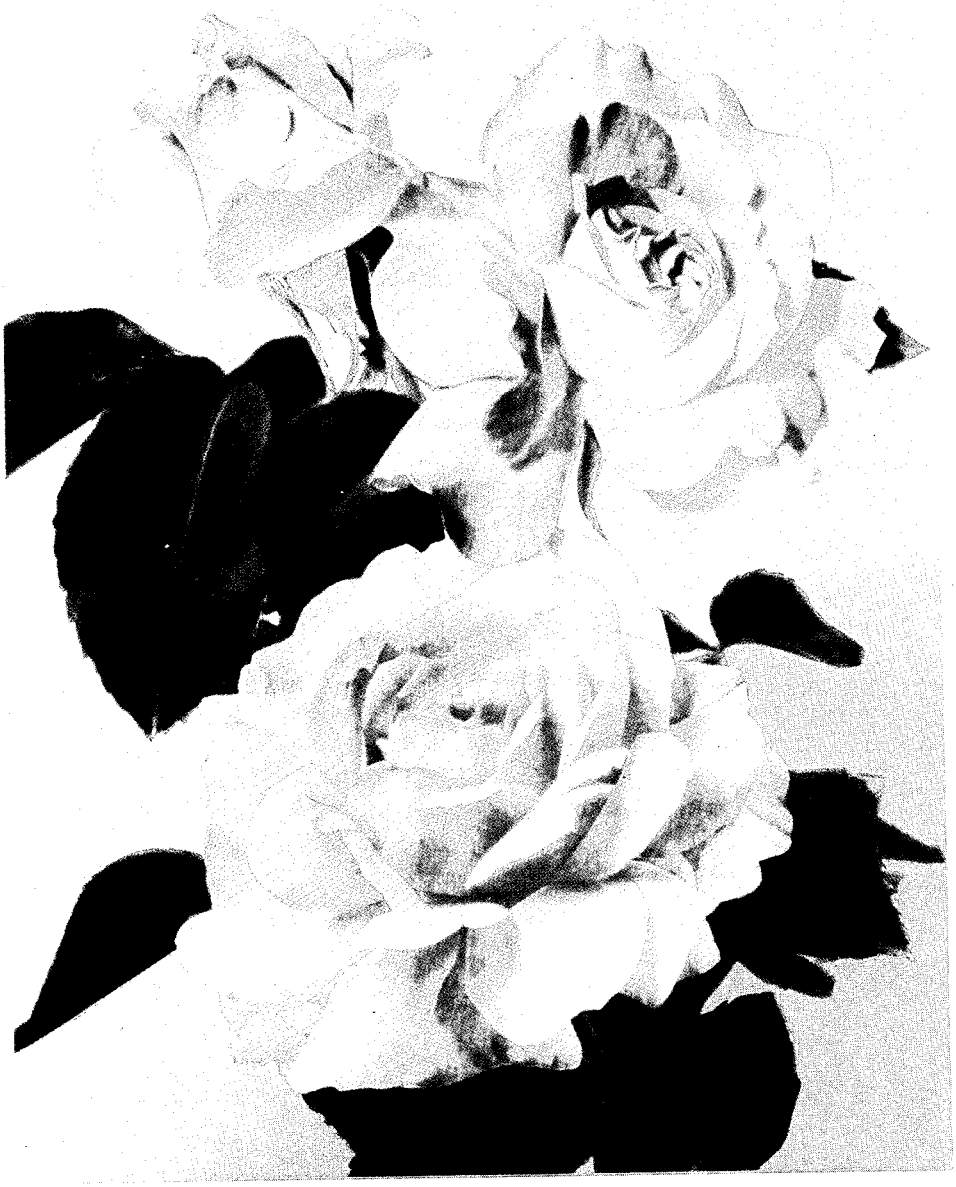
Inventor
Pedro Dot
By Robb & Robb
Attorneys Patented Apr. 16, 1940

UNITED STATES PATENT OFFICE

378

ROSE PLANT

Pedro Dot, Barcelona, Spain, assignor to Jackson & Perkins Company, Newark, N. Y.

Application August 10, 1939, Serial No. 289,483

1 Claim. (Cl. 47—61)

The present invention relates to a new and distinct variety of Hybrid Tea Rose plant, having as its primary feature of distinction the contrasting coloring of its blossom in the different stages of its development.

In respect to this coloring, the bud when the petals first divide is Scarlet Red, and when half open, the inside of the petals is Scarlet Red in contrast to the Peach Red of the reverse of said petals. As the flower opens full, the coloring reaches its most attractive range, with the top of the petals showing Rose Doree, the center Scarlet with a Lemon Yellow base on the inside, while on the reverse side Peach Red with Light Cadmium at the base predominates. Another attractive feature is found in the thickness of the petals and their velvety inside and satiny outside.

Other important features reside in the vigor of growth, the very large size of the flowers and foliage, the large short flat topped bud, the smooth edged branched sepals, and the double petalage of over thirty-five petals and few "rags" in the center.

Notably also, the flowers which are borne on long strong stems, are globular in form, flattening slightly at maturity.

The coloring and abundance of the foliage both young and old lend an attractive setting to the unusual coloring of the flowers above referred to.

Asexual reproduction of the new variety shows that the foregoing characteristics are fixed.

The following is a detail description of the new variety, all references to color being in accord with Ridgway's Color Standard.

Parentage:
*Seed parent.*—Luis de Briñas.
*Pollen parent.*—Catalonia.
Classification:
*Botanic and commercial.*—Hybrid Tea.

*Flower*

Observations made at Newark, New York, in the morning of June 30, 1938.

Blooming Habit:
*Recurrent.*—Continuous.

Bud:
*Size.*—Large.
*Form.*—Short with flat top. Is not affected by wet or hot weather.
*Color.*—When sepals first divide—Scarlet Red, Plate 1. When petals begin to unfurl—Scarlet, Plate 1. When half blown: inside of petals—Scarlet Red, Plate 1; reverse of petals—Peach Red, Plate 1.
*Sepals.*—Smooth edge, branched slightly. Curl back when half open.
*Calyx.*—Shape—apple. Size—large. Aspect—smooth.
*Peduncle.*—Length—medium. Aspect—prickly. Color—Cosse Green, Plate 5. Strength—stiff, heavy.
*Opening.*—Bud opens well. Is not affected by adverse conditions.

Bloom:
*Size.*—Large. Average size when fully expanded—5–5½''.
*Borne.*—Several together.
*Stems.*—Long, strong.
*Form.*—When first open—globular. Permanence—flattens very slightly.
*Petalage.*—Double (full but open center). Number of petals under normal conditions—35.
*Color.*—Center of flower—Scarlet Red, Plate 1. Outer petals—Scarlet, Plate 1. Base of petals (aiglet)—Lemon Yellow, Plate 4. Inside of petals, top of petal—Rose Doree, Plate 1; center of petal—Scarlet, Plate 1; base of petal—Lemon Yellow, Plate 4. Reverse of petals—Peach Red, Plate 1; base—Light Cadmium, Plate 4. General tonality from a distance—Orange Pink.
*Discoloration.*—General tonality at end of first day—Scarlet Red to Scarlet, Plate 1. Second day—Scarlet, Plate 1. Third day—Scarlet to Peach Red, Plate 1.

Petals:
*Texture.*—Thick. Is not affected by wet or hot weather.
*Appearance.*—Inside—velvety. Outside—satiny.
*Form.*—Oval, scalloped.
*Arrangement.*—Informal (with "rags" in center). Petaloids in center—many, small.
*Persistence.*—Drop off cleanly.
*Fragrance.*—Moderate. Nature—"Old Rose perfume."
*Lasting quality.*—On the plant and as cut flower—long.

Genital organs:
*Stamens, anthers.*—Large, many. Color—Flame Scarlet, Plate 2. Arrangement—regular around styles.
*Stamens, filaments (threads).*—Medium length. Color—Scarlet, Plate 1.
*Pollen.*—Cadmium Yellow, Plate 3.
*Styles.*—Bunched, uneven length; medium length, thin.
*Stigmas.*—Empire Yellow, Plate 4.
*Ovaries.*—Some protruding from calyx.

*Plant*

Form: Bush.
Growth: Very vigorous, branching.
Foliage: 5 to 7 leaflets.
*Size.*—Large.
*Quantity.*—Abundant.

*Color.*—New foliage: upper side—Light Elm Green, Plate 17, edges—Vandyke Red, Plate 13; under side—Biscay Green, Plate 17, edges—Vandyke Red, Plate 13. Old foliage: upper side—Elm Green, Plate 17; under side—Light Elm Green, Plate 17.

*Shape.*—Oval pointed.

*Texture.*—Upper side—glossy. Under side—smooth. Ribs and veins—prominent.

*Edge.*—Serrated (saw toothed).

*Serration.*—Single, small.

*Rachis.*—Cress Green, Plate 31. Under side—prickles.

*Stipules.*—Medium length, smooth.

*Disease resistance.*—Resistant.

Wood:

*New wood.*—Color—Light Cress Green, Plate 31. Bark—smooth.

*Old wood.*—Color—Cress Green, Plate 31. Bark—smooth.

Thorns (thorns are divided into thorns, prickles, and short needles):

*Thorns.*—Quantity: on main stalks from base and on laterals from stalk—many. Form—broad base, long, hooked downward. Color when young—Light Cress Green, Plate 31. Position—irregular.

*Prickles.*—Quantity: on main stalks—few; on laterals—many. Color—Light Cress Green, Plate 31.

I claim:

A new and distinct variety of Hybrid Tea Rose plant, characterized by its vigorous growth, size and unique coloring of the flowers and foliage, and the large short flat topped form of the bud and globular form of the flowers, substantially as shown and described.

PEDRO DOT.